(12) United States Patent
Liou et al.

(10) Patent No.: US 12,155,810 B2
(45) Date of Patent: Nov. 26, 2024

(54) COMPACT STEREOSCOPIC IMAGE CAPTURE UNIT

(71) Applicant: Intuitive Surgical Operations, Inc., Sunnyvale, CA (US)

(72) Inventors: Derek C. Liou, Cupertino, CA (US); Ian E. McDowall, Woodside, CA (US); Jonathan D. Halderman, Sunnyvale, CA (US); Doris Lin, Santa Clara, CA (US); John A Barton, Mountain View, CA (US); Bruce M. Schena, Menlo Park, CA (US); Kierstin Gray Parrish, Boulder Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1013 days.

(21) Appl. No.: 17/254,075

(22) PCT Filed: Jun. 26, 2019

(86) PCT No.: PCT/US2019/039350
§ 371 (c)(1),
(2) Date: Dec. 18, 2020

(87) PCT Pub. No.: WO2020/006149
PCT Pub. Date: Jan. 2, 2020

(65) Prior Publication Data
US 2021/0266517 A1 Aug. 26, 2021

Related U.S. Application Data

(60) Provisional application No. 62/691,958, filed on Jun. 29, 2018.

(51) Int. Cl.
*H04N 13/239* (2018.01)
*A61B 1/00* (2006.01)
(Continued)

(52) U.S. Cl.
CPC ....... *H04N 13/239* (2018.05); *A61B 1/00193* (2013.01); *A61B 1/05* (2013.01);
(Continued)

(58) Field of Classification Search
CPC ............ H04N 13/239; H04N 2213/001; A61B 1/00193; A61B 1/05; A61B 1/313;
(Continued)

(56) References Cited

U.S. PATENT DOCUMENTS 9,455,292 B2 * 9/2016 Luan ................. H01L 27/14685
2010/0200898 A1 8/2010 Lin et al.
(Continued)

FOREIGN PATENT DOCUMENTS

CN 103702602 A 4/2014
CN 108463771 A 8/2018
(Continued)

OTHER PUBLICATIONS

International Preliminary Report on Patentability for Application No. PCT/2019/039350, mailed on Jan. 7, 2021, 8 pages.
(Continued)

*Primary Examiner* — Jacob R Crum

(57) ABSTRACT

An image capture unit has mounted in a frame: a first imaging assembly, a first circuit board, a second imaging assembly, and a second circuit board. The first imaging assembly is mounted on the first circuit board. The second imaging assembly is mounted on the second circuit board. A portion of the first circuit board and a portion of the second circuit board have a stacked configuration with the portion of the first circuit board being approximately parallel to the portion of the second circuit board. An end of another portion of the first circuit board is adjacent to an end of another portion of the second circuit board.

12 Claims, 4 Drawing Sheets

(51) Int. Cl.
*A61B 1/05* (2006.01)
*A61B 1/313* (2006.01)
*H05K 1/02* (2006.01)
*H05K 1/14* (2006.01)

(52) U.S. Cl.
CPC .............. *A61B 1/313* (2013.01); *H05K 1/028* (2013.01); *H05K 1/144* (2013.01); *H04N 2213/001* (2013.01); *H05K 2201/10151* (2013.01)

(58) Field of Classification Search
CPC .... A61B 1/00105; A61B 1/051; H05K 1/028; H05K 1/144; H05K 2201/10151
See application file for complete search history.

(56) References Cited

U.S. PATENT DOCUMENTS

| | | | | |
|---|---|---|---|---|
| 2013/0293751 A1* | 11/2013 | Vaartstra | .............. | H04N 23/843 438/70 |
| 2014/0078387 A1* | 3/2014 | Tao | ........................ | H04N 23/57 348/374 |
| 2015/0163937 A1 | 6/2015 | McClatchie et al. | | |
| 2017/0095142 A1 | 4/2017 | McDowall | | |
| 2017/0112369 A1 | 4/2017 | Czupalla et al. | | |
| 2017/0280969 A1 | 10/2017 | Levy et al. | | |
| 2021/0318507 A1* | 10/2021 | Oh | ........................ | G02B 7/003 |

FOREIGN PATENT DOCUMENTS

| | | |
|---|---|---|
| EP | 2752147 A1 | 7/2014 |
| WO | WO-2017122971 A1 | 7/2017 |

OTHER PUBLICATIONS

International Search Report and Written Opinion for Application No. PCT/US2019/039350, mailed on Jan. 7, 2020, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

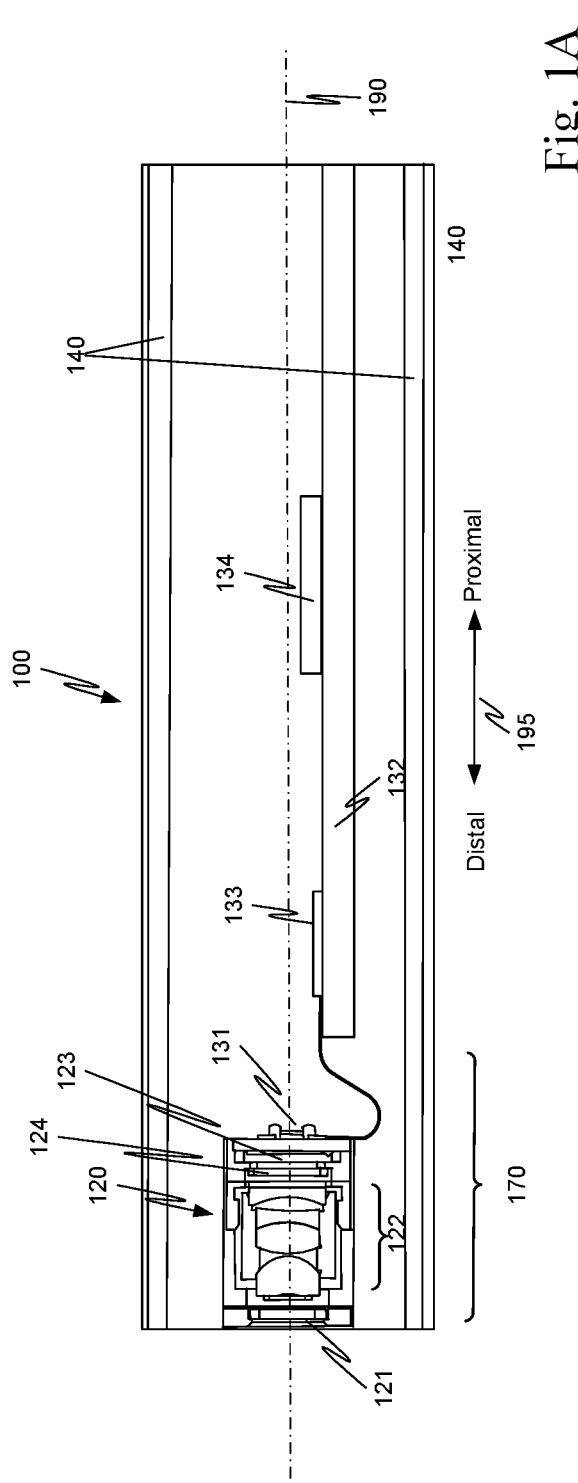
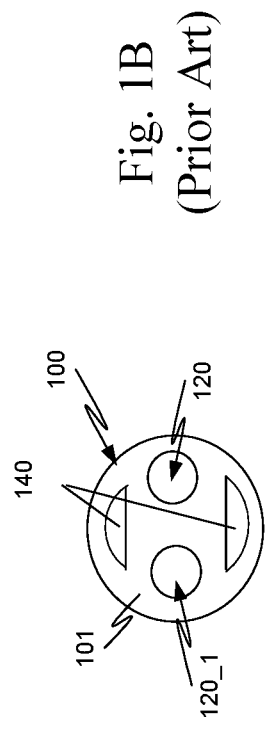
Fig. 1A
(Prior Art)
Fig. 1B
(Prior Art)

COMPACT STEREOSCOPIC IMAGE CAPTURE UNIT

RELATED APPLICATIONS

The present application claims priority to U.S. Provisional Patent Application No. 62/691,958, filed on Jun. 29, 2018, and entitled "A COMPACT STEREOSCOPIC IMAGE CAPTURE UNIT," the contents of which are hereby incorporated by reference in their entirety.

BACKGROUND OF THE INVENTION

Field of the Invention

The present invention relates generally to image capture units, and more particularly to an image capture unit mounted in a distal tip of an endoscope or a laparoscope.

Description of Related Art

Endoscopes and laparoscopes used in minimally invasive surgery may come in various tip angles. Two common tip angles are a zero degree angle and a thirty degree angle. A stereoscopic endoscope used in minimally invasive surgery includes two optical channels, which typically are identical in construction.

FIG. 1A is an illustration of a portion of a distal body portion of a zero degree endoscope 100. FIG. 1B is an illustration of a distal face 101 of the body portion of FIG. 1A.

An image capture unit 120 is mounted in a distal portion 170 of endoscope 100. Image capture unit 120 includes a window 121, an objective lens system 122, and an image sensor 123. Note that window 121 is perpendicular to lengthwise axis 190 of endoscope 100. Endoscope 100 also includes illumination light channels 140.

Image capture unit 120 can include one or more filters to process light that is captured by image sensor 123. Also, image capture unit 120 can optionally include a color filter array, such as a Bayer pattern color filter array, as part of image sensor 123. Image sensor 123 includes a cover window 124 in the distal face of image sensor 123. This permits manufacture of image sensor 123 in a separate facility from where image sensor 123 is assembled with objective lens system 122, because cover window 124 prevents any debris from entering image sensor 123. Image capture unit 120 includes a stop proximal to window 121 and distal to and adjacent to a distal end of objective lens system 122.

Image capture unit 120 is coupled to a printed circuit board interface 131. Printed circuit board interface 131 in turn is coupled to a printed circuit board 132 by a flexible circuit. Analog to digital integrated circuit 133 and transmission integrated circuit 134 are mounted on printed circuit board 132. Analog to digital integrated circuit 133 is coupled to image capture unit 120 and is coupled to a transmission integrated circuit 134. Transmission integrated circuit 134 converts the electric digital signals to optical signals for transmission over a fiber optic cable.

Endoscope 100 includes a second channel 120-1 that is identical to the channel illustrated in FIG. 1A, i.e., the two channels are side-by-side. The second channel is hidden behind the channel illustrated in FIG. 1A. In FIG. 1A the distal and proximal directions are indicated by arrow 195.

SUMMARY

A stereo camera, sometimes referred to as an image capture unit, includes two independent imaging electronics boards, e.g., two circuit boards, mounted in a frame. In one aspect, this image capture unit includes a first imaging assembly, a first circuit board, a second imaging assembly, and a second circuit board. The first imaging assembly is mounted on the first circuit board. The second imaging assembly is mounted on the second circuit board. A portion of the first circuit board and a portion of the second circuit board have a stacked configuration with the portion of the first circuit board being approximately parallel to the portion of the second circuit board. The mounting of two independent imaging electronics boards (the first and second circuit boards) in the frame in a stacked configuration uses the available space more efficiently, and so reduces the volume required to house two independent imaging electronics boards.

Also, an end of another portion of the first circuit board is adjacent to an end of another portion of the second circuit board. In this configuration, the first imaging assembly being mounted on the first circuit board is the first imaging assembly being mounted on the another portion of the first circuit board. Similarly, the second imaging assembly being mounted on the second circuit board is the second imaging assembly being mounted on the another portion of the second circuit board.

By employing flex circuit construction and mechanical parts, a design that requires a minimum amount of space is realized. In this aspect, the first circuit board includes a first rigid circuit board portion, a flex circuit board portion, and a second rigid circuit board portion. The flex circuit board portion is positioned between the first rigid circuit board portion and the second rigid circuit board portion. The portion of the first circuit board, previously referred to, in this aspect is the first rigid circuit board portion. Also, the second circuit board includes a first rigid circuit board portion, a flex circuit board portion, and a second rigid circuit board portion. The flex circuit board portion of the second circuit board is positioned between the first rigid circuit board portion of the second circuit board and the second rigid circuit board portion of the second circuit board. The portion of the second circuit board, referred to above, in this aspect is the first rigid circuit board portion of the second circuit board.

The image capture unit also has a lengthwise axis. In this aspect, the second rigid circuit board portion of the first circuit board and the second rigid circuit board portion of the second circuit board are approximately perpendicular to the lengthwise axis of the image capture unit.

In addition to two independent imaging electronics boards, in one aspect, the image capture unit includes an objective lens apparatus and a window mounted in the frame. In a zero degree apparatus, e.g., an endoscope or a laparoscope, including the stereo camera, a plane including a surface of the window is at angle to a plane including a distal face of objective lens apparatus so that the two planes intersect. This reduces artifacts caused by stray reflected light in captured images.

In one aspect, a perimeter of a proximal portion of a circuit board of the stereo camera is hermetically sealed to a wall of the frame. This prevents any fluids from entering the interior volume including the imaging electronics boards of the stereo camera during sterilization In another aspect, an image capture unit includes first and second imaging assemblies and first and second rigid circuit flex boards. The first imaging assembly includes a first end and a first imaging surface, and the second imaging assembly includes a second end and a second imaging surface. The first imaging surface is aligned with the second imaging surface. The first rigid flex circuit board is coupled to the first imaging assembly, and the first rigid flex circuit board has a first surface. The first imaging surface is perpendicular to the first surface of the first rigid flex circuit board. The second rigid flex circuit board is coupled to the second imaging assembly, and the second rigid circuit board has a second surface corresponding to the first surface of the first rigid flex circuit board. The second imaging surface is perpendicular to the second surface of the second rigid flex circuit board. The first surface of the first rigid circuit flex board is approximately parallel to the second surface of the second rigid circuit board. The first and second surfaces are approximately parallel to and on opposite sides of a lengthwise axis of the image capture unit. In one aspect, the first surface of the first rigid circuit board is separated from the second surface of the second rigid circuit board by a known distance with the first end of the first imaging assembly adjacent to the second end of the second imaging assembly.

In one aspect, the image capture unit also includes a first objective lens system and a second objective lens system. The first objective lens systems is configured to focus a first image on the first imaging assembly, while the second objective lens system is configured to focus a second image on the second imaging assembly.

A window of the image capture unit includes a surface. The surface of the window is at an angle to the lengthwise axis of the image capture unit. In one aspect, the angle is twelve degrees.

The image capture unit also includes a frame having mounted therein the first and second image assemblies and the first and second circuit boards, where at least one of the first and second circuit boards is hermetically sealed to the frame. In one aspect, the image capture unit includes a support wall and a wall. The first circuit board has a metal trace around an outer perimeter. The support wall is affixed to the metal trace to form a hermetic seal, and the support wall is affixed to the wall. In one aspect, the support wall is affixed to the metal trace by a solder joint, and the support wall is affixed to the wall by an electro-weld.

A method includes affixing a metal trace around a perimeter of a circuit board in an image capture unit to a support wall to form a hermetic seal. The method also includes affixing the support wall to a wall of the image capture unit. In one aspect, the affixing a metal trace around a perimeter of a circuit board in an image capture unit to a support wall includes soldering the metal trace to the support wall. The affixing the support wall to a wall of the image capture unit includes electro-welding the support wall to the wall of the image capture unit.

In yet another aspect, an apparatus includes an objective lens system and a window. The objective lens system is mounted in a distal end of the apparatus, and the objective lens system includes a lengthwise axis. A window is mounted in a distal face of the apparatus. The window has a surface oriented at an angle to the lengthwise axis of the objective lens system. In one aspect, the angle is twelve degrees.

In still another aspect, an image capture unit includes a support wall having an opening, and a frame having a wall. The image capture unit has a circuit board mounted in the frame. The circuit board includes a metal trace around an outer perimeter of the circuit board. An end of the circuit board passes through the opening and the support wall is affixed to the metal trace to form a hermetic seal. The support wall is affixed to the wall.

BRIEF DESCRIPTION OF THE DRAWINGS

FIG. 1A is an illustration of a distal body portion of a prior art zero degree endoscope.

FIG. 1B is an illustration of the distal face of the distal body portion of FIG. 1A.

Figure 2A:
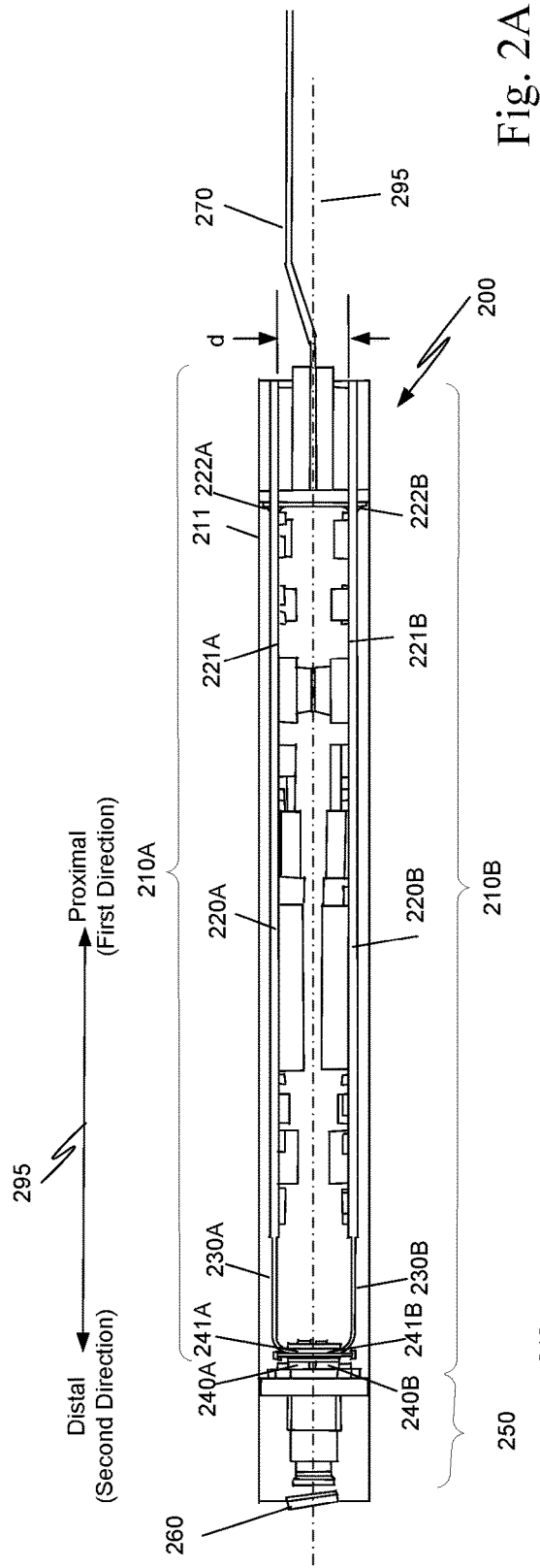
FIG. 2A is an illustration of a compact image capture unit that includes two independent imaging electronics boards mounted in a frame.

In the drawings, the first digit of a reference number indicates the figure in which the element with that reference number first appeared.

DETAILED DESCRIPTION

Stereo cameras for minimally invasive surgical applications typically need to be packaged in a small round tube with dimensions similar to that of a ballpoint pen. Fitting a pair of cameras in such a space is challenging.

To overcome this challenge, a stereo camera 200 (FIG. 2A), sometimes referred to as image capture unit 200, includes two independent imaging electronics boards 210A, 210B mounted in a frame 211. Imaging electronics boards 210A, 210B include a first circuit board and a second circuit board, respectively. Imaging electronics board 210A also includes a first imaging assembly 240A, and imaging electronics board 210B includes a second imaging assembly 240B.

The two independent imaging electronics boards 210A, 210B are mounted in a frame 211 so that a portion 220A of imaging electronics board 210A and a portion 220B of imaging electronics board 210B have a stacked configuration. In the stacked configuration, surface 221A of portion 220A of the first circuit board faces a corresponding surface 221B of portion 220B of the second circuit board, as illustrated in FIG. 2A, and conversely.

Surface 221A of imaging electronics board 210A is equivalent to surface 221B of imaging electronics board 210B, because surface 221 (FIG. 2B) represents surfaces 221A and 221B relative to their respective imaging electronics board. Thus, the two surfaces are said to be corresponding surfaces. Similarly, a surface of portion 230A corresponds to a surface of portion 230B and the two surface face each other in the stacked configuration, as illustrated in FIG. 2A.

In one aspect, the stacked configuration results in a portion 220A of the first circuit board of imaging electronics board 210A being approximately parallel to portion 220B of the second circuit board of imaging electronics board 210A. For example, surface 221A of portion 220A is approximately parallel to corresponding surface 221B of portion 220B. Also, in the stacked configuration, surfaces 221A and 221B are each approximately parallel to lengthwise axis 295 and are on opposite sides of lengthwise axis 295.

Also, as shown in FIG. 2A, an end of another portion 241A of the first circuit board of imaging electronics board 210A is adjacent to an end of another portion 241B of the second circuit board of imaging electronics board 210B. In this example, first imaging assembly 240A is mounted on another portion 241A of the first circuit board of imaging electronics board 210A. Also, second imaging assembly 240B is mounted on another portion 241B of the second circuit board of imaging electronics board 210B.

By employing flex circuit construction and mechanical parts, a design that requires a minimum amount of space is realized. With respect to the flex circuit construction, each of imaging electronics boards 210A, 210B includes a single rigid flex circuit board. In one aspect, imaging electronics boards 210A and 210B are identical, and single rigid flex circuit board 205, illustrated in FIG. 2B, represents both imaging electronics boards 210A and 210B.

Figure 2B:
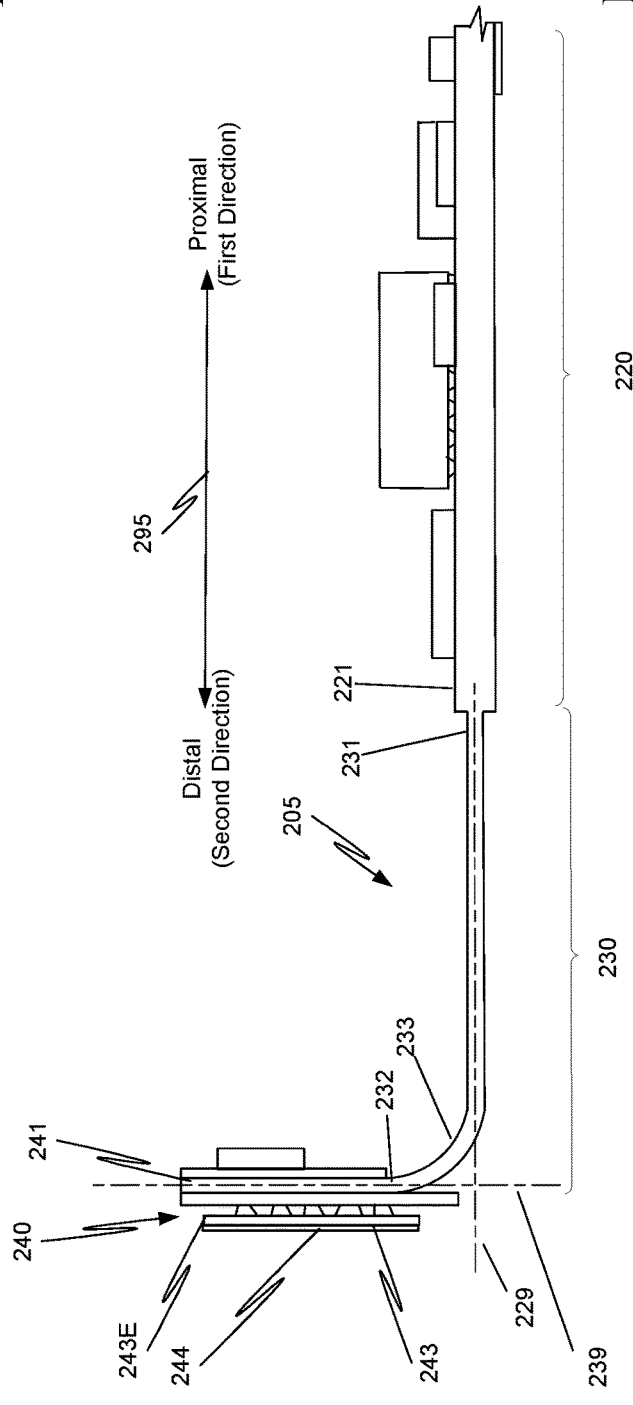
FIG. 2B is an enlarged illustration of a portion of the two independent imaging electronics boards of FIG. 2A.

Single rigid flex circuit board 205 of FIG. 2B includes a first rigid circuit board portion 220 (FIG. 2B) (referred to above as portion 220A and portion 220B), a flexible circuit board portion 230, and a second rigid circuit board portion 241 (referred to above as another portion 241A and another portion 241B). The two rigid circuit board portions 220, 241 are joined by a flexible circuit board portion 230. Flexible circuit board portion 230 has a single bend between the two rigid circuit board portions 220, 241. The two rigid circuit board portions 220, 241 are mounted in frame 211 so that two rigid circuit board portions 220, 241 are about perpendicular to each other. Thus, the angle between the two rigid circuit board portions 220, 241 is a right angle. (See FIG. 2B) The single bend made by flexible circuit board portion 230 is referred to as a right angle bend since it joins the two rigid circuit board portions 220, 241 that are at a right angle to one another. In one aspect, to make flexible circuit board portion 230, a portion of one or more layers of the rigid flex circuit board 205 is sacrificed, e.g., removed, to define flexible circuit board portion 230.

The mounting of two independent imaging electronics boards 210A, 210B (FIG. 2A) in frame 211 in a stacked configuration—with one first rigid circuit board portion 220A mounted over and above the other first rigid circuit board portion 220B, as opposed to a side-by-side orientation—uses the available space more efficiently, and so reduces the volume required to house two independent imaging electronics boards 210A, 210B. Also, one second rigid circuit board portion 241A has an end adjacent to an end of other second rigid circuit board portion 241B.

In addition to two independent imaging electronics boards 210A, 210B, an objective lens apparatus 250 and a window 260 are mounted in frame 211. In a typical zero degree endoscope, as illustrated in FIG. 1A, the surfaces of window 121 are parallel with a distal end of objection lens system 122. However, in a zero degree apparatus including image capture unit 200, e.g., a zero degree endoscope or a zero degree laparoscope, a plane including a surface of window 260 is an at angle to a plane including a distal face of an objective lens system in objective lens apparatus 250 so that the two planes intersect, i.e., are not parallel. This reduces artifacts caused by stray reflected light in the captured images.

In one aspect, a perimeter of a proximal portion of each of first rigid circuit board portions 220A, 220B of image capture unit 200 is hermetically sealed to a wall of frame 211. During sterilization, this prevents any fluids from entering the interior volume including the imaging electronics boards of image capture unit 200.

In this aspect, a first imaging electronics board 210A includes a first rigid flex circuit board 205. The first rigid flex circuit board includes a first rigid circuit board portion 220A, a flexible circuit board portion 230A, and a second rigid circuit board portion 241A. Second imaging electronics board 210B includes a second rigid flex circuit board 205. The second rigid flex circuit board includes a first rigid circuit board portion 220B, a flexible circuit board portion 230B, and a second rigid circuit board portion 241B.

A first imaging assembly 240A is mounted on second rigid circuit board portion 241A of first imaging electronics board 210A. A second imaging assembly 240B is mounted on second rigid circuit board portion 241B of second imaging electronics board 210B. First and second imaging electronic boards 210A, 210B are mounted in frame 211 so that a first imaging surface (a surface of the image sensor) of first imaging assembly 240A is aligned with and adjacent to a second imaging surface (a surface of the image sensor) of second imaging assembly 240B. The first and second imaging surfaces are approximately perpendicular to lengthwise axis 295, in this aspect.

First and second imaging electronics boards 210A, 210B also are mounted in frame 211 so that a surface 221A of first rigid circuit board portion 220A of first imaging electronics board 210A is approximately parallel to a corresponding surface 221B of first rigid circuit board portion 220B of second imaging electronics board 210B. In one aspect, surface 221A is separated from surface 221B by a known distance d. Each of surfaces 221A and 221B is approximately parallel to a lengthwise axis 295 of image capture unit 200, and so each of first rigid circuit board portion 220A and first rigid circuit board portion 220B is approximately parallel to lengthwise axis 295, sometimes referred to as longitudinal axis 295. The mounting of two independent imaging electronics boards 210A, 210B in frame 211 in a stacked configuration—one board over and above the other, as opposed to a side-by-side orientation as in FIG. 1—uses the available space more efficiently, and so reduces the volume required to house two independent imaging electronics boards 210A, 210B.

Herein, approximately parallel, substantially parallel, about parallel, and like terms mean parallel to within manufacturing tolerance associated with the rigid flex circuit boards, the frame, and the mounting of the rigid flex circuit boards in the frame. Similarly approximately perpendicular, substantially perpendicular, about perpendicular, and like terms mean perpendicular to within manufacturing tolerance associated with the rigid flex circuit boards, the frame, and the mounting of the rigid flex circuit boards in the frame.

As noted above, image capture unit 200 also includes an objective lens apparatus 250 and a window 260 mounted in frame 211. Objective lens apparatus 250 is mounted in a distal portion of frame 211, and window 260 is mounted in a distal face of frame 211. Objective lens apparatus 250 includes a first (left) objective lens system and a second (right) objective lens system. In another aspect, each objective lens system has its own tilted window. Each of the objective lens systems focuses an image on a surface of an image sensor in the corresponding imaging assembly (see FIG. 2B). In one aspect, the objective lens systems are equivalent to those disclosed in PCT International Publication No. WO 2015/142797 A1 (published 24 Sep. 2015, disclosing "Angled Endoscope Tip Image Capture Unit."), and so are not considered in further detail.

Unlike a typical objective lens system in a zero degree endoscope where the surfaces of a window for the objective lens system are parallel with the distal end of the objection lens apparatus 250, a plane including a surface of window 260 in a zero degree endoscope is an at angle to a plane including a distal face of an objective lens systems in objective lens apparatus 250 so that the two planes intersect. As explained more completely below, this reduces artifacts caused by stray reflected light in captured images.

Image capture unit 200 is mounted in a distal end of an endoscope or a distal end of a laparoscope. As is known, such a device typically must be sterilized after each use. Thus, in one aspect, a perimeter 222A, 222B of a proximal portion of each of first rigid circuit board portions 220A, 220B is hermetically sealed to a wall of frame 211. During sterilization, this prevents any fluids from entering the interior volume of frame 211, in which imaging electronics boards 210A, 210B are mounted.

First rigid circuit board portions 220A and 220B have mounted thereon components that process image data from imaging assemblies 240A and 240B, and that transfer the processed image data over a ribbon cable 270. In one aspect, the components perform a format and level conversion on the image data from imaging assemblies 240A and 240B.

A connector on an end of ribbon cable 270 connects to each of first rigid circuit board portions 220A and 220B. Ribbon cable 270 includes pathways to simultaneously transfer signals from both first rigid circuit board portions 220A and 220B.

FIG. 2B is an enlarged view of a distal portion of imaging electronics boards 210A, 210B. As noted above, imaging electronics boards 210A, 210B are identical. Thus, the following discussion of imaging electronics board 210 applies to each of imaging electronics boards 210A, 210B.

Imaging assembly 240 is mounted on second rigid circuit board portion 241 of rigid flex circuit board 205. Imaging assembly 240 optionally includes a color filter array, such as a Bayer pattern color filter array, as part of image sensor 243. Image sensor 243 includes a cover window 244 on a distal face of image sensor 243. The distal face—an imaging surface—of image sensor 243 is perpendicular to surface 221 of first rigid circuit board portion 220, stated in another way, a face of imaging assembly 240 is perpendicular to first rigid circuit board portion 220.

An end 243E of image sensor 243 farthest from surface 221, e.g., farthest from first rigid circuit board portion 220, is adjacent to an end of the other image sensor in image capture unit 200, as illustrated in FIG. 2A, when imaging assemblies 240A, 240B are mounted in frame 211. In one aspect, image capture unit 200 includes a stop proximal to window 260 and proximal to and adjacent to a proximal end of the objective lens system in objective lens apparatus 250.

In this aspect, a first end 231 of flexible circuit board portion 230 is at a right angle to a second end 232 of flexible circuit board portion 230. Specifically, an extended centerline 229 of first end 231 intersects an extended center line 239 of second end 232 at a right angle. Also, an extended centerline of first rigid circuit board portion 220 is at a right angle to an extended centerline of second rigid circuit board portion 241. The right angle is formed with only a single bend 233 in flexible circuit board portion 230. In one aspect, to implement single right angle bend 233, layers of the rigid flex circuit board 205 are sacrificed, e.g., removed, to define flexible circuit board portion 230.

Removal of the sacrificial layers facilitate forming single bend 233 without affecting the performance of rigid flex circuit board 205. In this aspect, the sacrificial layers are a portion of rigid flex circuit board 205 that would have the largest radius, e.g., the layers that would have been on the outer side of single bend 233, if not removed. Reducing the number of layers in a region of rigid flex circuit board 205 assists in giving that region the flexibility needed to form right angle bend 233. Hence, the rigid portions of rigid flex circuit board 205 are not susceptible to bending and are not bent during use, while the flex portion of rigid flex circuit board 205 is bent during use so that the centerlines of the ends of the flex portion define a right angle, in this aspect.

To further facilitate single bend 233 without affecting the performance of rigid flex circuit board 205, ground planes of rigid flex circuit board 205 are cross hatched instead of being solid. The cross hatched ground planes maintain a ground reference for high speed differential pair signals. In one aspect, the flexible circuit board portion has seven layers while the rigid circuit board portions have nine layers. In other aspects, the flexible circuit board portion has at least one layer less than the rigid circuit board portions.

Hence, in this aspect, image capture unit 200 includes a rigid flex circuit board 205 that in turn includes a second rigid circuit board portion 241, on which imaging assembly 240 is mounted, and a first rigid circuit board portion 220 that are joined by a flexible circuit board portion 230. When mounted in frame 211, flexible circuit board portion 230 has a single right angle bend 233 between first and second rigid circuit board portions 220, 241.

Figure 3A:
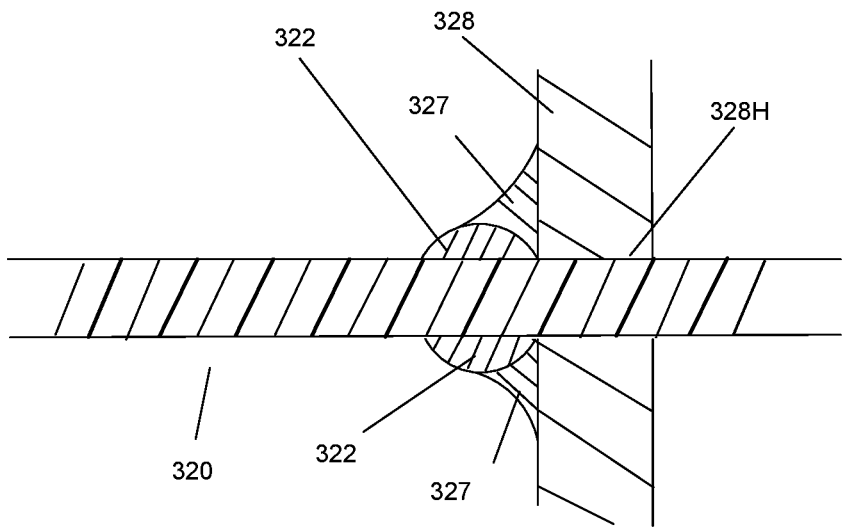
FIGS. 3A and 3B are cutaway diagrams of a portion of an image capture unit, which illustrate the details of forming a hermetic seal about a circuit board.
Figure 3B:
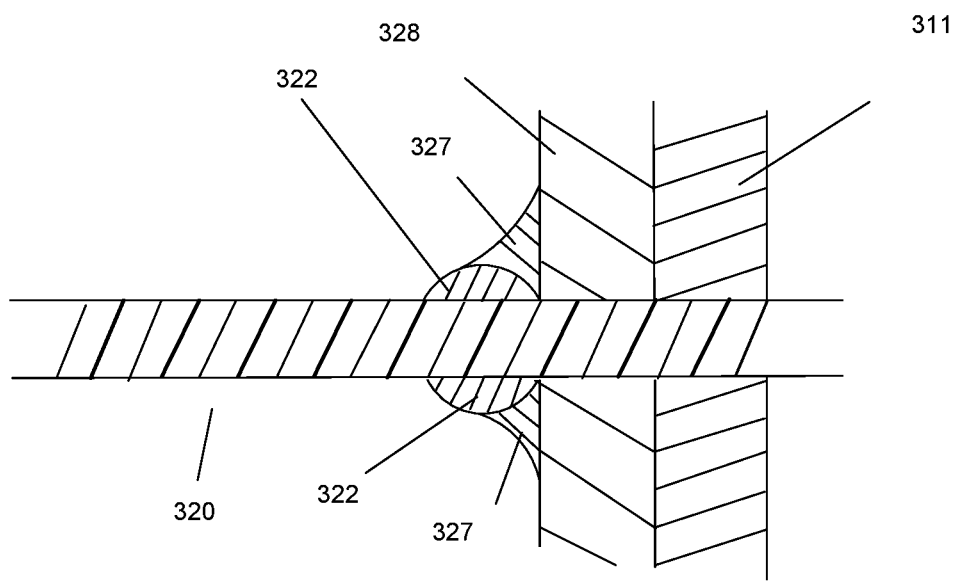

FIGS. 3A and 3B are cutaway diagrams of a portion of an image capture unit, e.g., image capture unit 200, which illustrate the details of forming a hermetic seal about a circuit board 320. Circuit board 320 includes a metal trace 322, e.g., a gold trace, which extends around the outside perimeter of circuit board 320.

Circuit board 320 is passed through a hole 328H in a support wall 328. In one aspect, hole 328H has the same shape as the perimeter of circuit board 320 and is large enough to permit passage of circuit board 320 through hole 328H without damaging circuit board 320. Circuit board 320 is passed through hole 328H until metal trace 322 abuts support wall 328, or is partially within hole 328H.

With circuit board 320 positioned properly in hole 328H, a solder joint 327 is formed between a surface of support wall 328 around hole 328H and metal trace 322. Solder joint 327 forms a hermetic seal between support wall 328 and circuit board 320 around the perimeter of circuit board 320.

Circuit board 320 is optionally passed through a hole in a wall of a frame 311 of the image capture unit. In one aspect, after circuit board 320 is soldered to support wall 328, support wall 328 is electro-welded to the wall of frame 311.

In one aspect, the environment in which image capture unit 200 is used is unique in the following ways: the light source illuminating the scene is typically located close to image capture unit 200 much like a headlamp; the objects being viewed through image capture unit 200 are moving and relatively close to image capture unit 200; the objects include wet tissue surfaces and highly reflective stainless steel; and there is a need to see in great detail and with a minimum of artifacts.

Several of these aspects place great demands on the ability to control stray light. Reflections internally to the objective lens system can cause artifacts in all or part of the image. Typically, these reflections are controlled through the use of coatings on the optical surfaces, which reduce the reflection of light at those optical surfaces. In a typical camera lens, each element receives a coating specific to the wavelength range being imaged and the angle of incidence of the light at that surface.

A unique aspect of imaging systems used inside the body and re-used is that they are aggressively cleaned, disinfected, and sterilized between uses. These processes can be very aggressive leading to degraded imaging quality if the window through which the images are captured becomes scratched. Thus, sapphire, one of the hardest materials known, may be used in window 260. In addition, the outer surface of sapphire window 260 is ideally not coated in any way as the coating material is less durable than the sapphire and is thus subject to scratching and abrasion or chemical attack. If the coating becomes damaged, the captured images are degraded in much the same way as scratches on eye glasses results in hazy vision.

Figure 4A:
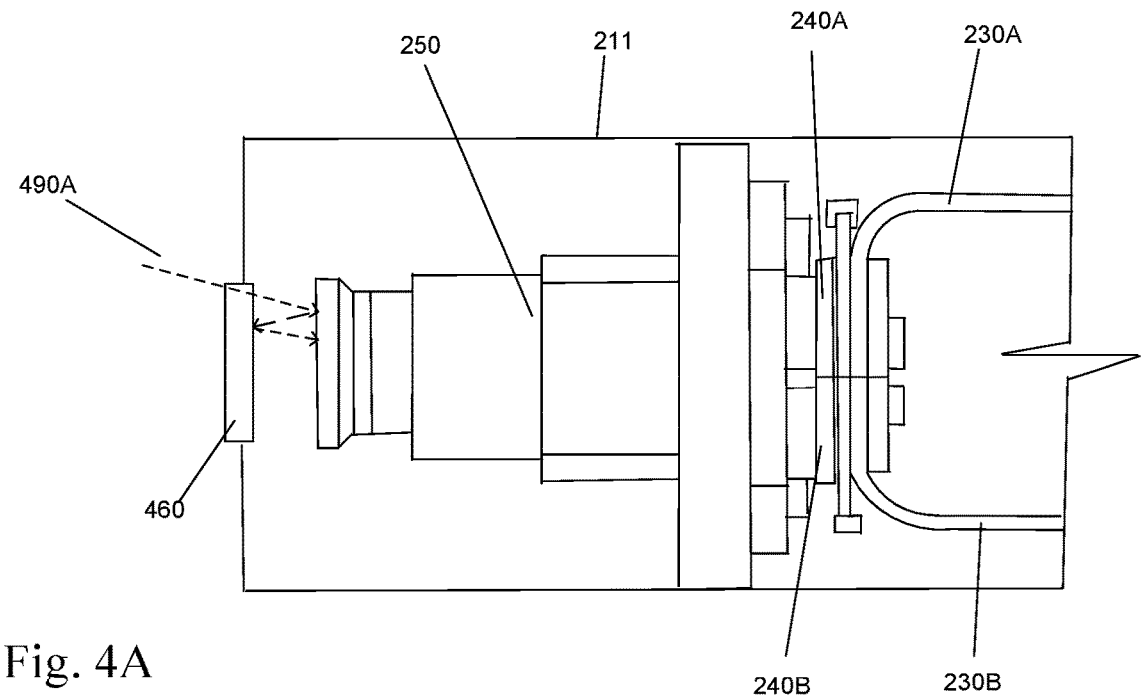
FIG. 4A is an illustration of a distal portion of a first image capture unit 400.

It has been observed that the high refractive index difference between sapphire window 260 and air results in an interface at which reflections occur and the reflections create artifacts in the captured images. FIG. 4A is an illustration of a distal portion of an image capture unit 400. Image capture unit 400 is the same as image capture unit 200 except window 460 is not tilted.

Light 490A passes through window 460 and is reflected by structure in an objective lens system of objective lens apparatus 250 back towards window 460. As just described, window 460 is made of sapphire and the high refractive index difference between sapphire window 460 and air causes window 460 to act like a mirror that reflects the reflected light back into the field of view of the objective lens system. Thus, the twice reflected light is captured as an artifact in a captured image.

Figure 4B:
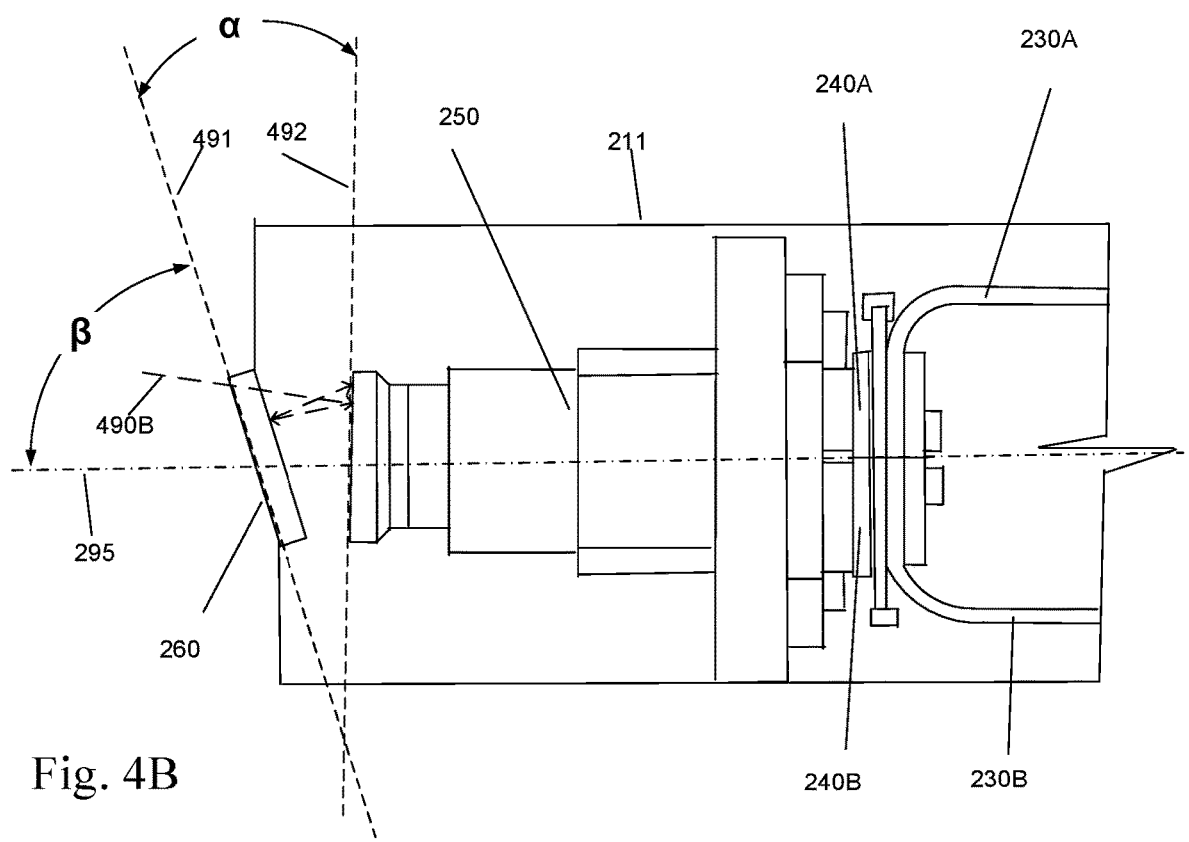
FIG. 4B is an illustration of a distal portion of the image capture unit of FIG. 2A.

In contrast, in image capture unit 200 (FIG. 4B), window 260 is tilted at an angle to the distal face of the objective lens system in objective lens apparatus 250. The tilt of window 260 can be specified in several different ways. For example, a face of window 260 is in a first plane 491 that intersects with lengthwise axis 295 (which is in a different plane) of image capture unit 200 at an angle β, which defines the tilt of window 260. Alternatively, a face of window 260 is in a first plane 491 and a distal face of the objective lens system in objective lens apparatus 250 is in a second plane 492. First plane 291 and second plane 292 intersect at an angle α, which provides a second definition of the tilt of window 260.

In one aspect, the tilt of window 260 is empirically determined by trying a range of angles for the tilt and observing which angle results in a captured image with the least artifacts associated with reflected light, or alternatively results in a captured image with reduced artifacts and artifacts associated with reflected light located in a region or regions of the captured image that do not affect the overall quality of the image from a user's prospective, e.g., in the outer boundaries of the image that are not typically used in clinical assessments. In one aspect the tilt is in a range for angle β from one degree to forty-five degrees, and in one aspect twelve degrees.

With a tilted window, light 490B passes through window 260 and is reflected by structure in objective lens apparatus 250 back towards window 260. Window 260 is made of sapphire and the high refractive index difference between sapphire window 260 and air causes window 260 to act like a mirror that reflects the reflected light. However, instead of re-reflecting the light into the field of view of objective lens apparatus 250, the tilt of window 260 causes window 260 to reflect the reflected light out of the field of view, and so no artifacts are created in the captured image due to light reflected by window 260. In some aspects, the re-reflected light may be within the field of view of objective lens apparatus 250, but is captured in a portion of the image that is not of clinical interest, and so the resulting artifact does not degrade the portion of the image of interest to a clinician. Thus, when image capture unit 200 is mounted in the distal end of a zero-degree endoscope or a zero-degree laparoscope, problems with light reflected by window 260 into objective lens apparatus 250 are minimized.

The design of image capture unit 200 also provides for fabrication requirements. In one aspect, image capture unit 200 is fabricated as follows:

- A printed circuit board is made with two rigid circuit board portions 241, 220 joined by a flexible circuit board portion 230;
- The printed circuit board is populated with electronic components and the image sensor to form an imaging electronics board 210;
- Imaging electronics board 210 is tested for functionality before the next assembly act;
- A pair of imaging electronics boards 210 are assembled into a frame 211 with the sensor cover windows 244 being used as the references;
- Frame 211 is also used as the reference surface for the placement and alignment of the objective lens systems; and
- Frame 211 provides for a V-shaped grove along which the objective lens systems may be slid to align for focus.

By using a single machined part, frame 211, for referencing cover windows 244 and the objective lens systems, the stack up of mechanical tolerance is reduced. Additionally, the assembly can place the two image sensors very close to each other and reference them in such a way as to account for placement variation that may occur during the soldering process used to affix the imaging sensor to the printed circuit board.

Herein, all examples and illustrative references are non-limiting and should not be used to limit the claims to specific implementations and embodiments described herein and their equivalents. In view of this disclosure, particular features described in relation to one aspect or embodiment may be applied to other disclosed aspects or embodiments of the invention, even though not specifically shown in the drawings or described in the text.

Herein, first, second, etc. are used as adjectives to distinguish between elements and are not intended to indicate a number of elements or any particular ordering of the elements. Also, top, bottom, and side are used as adjectives to aid in distinguishing between elements as viewed in the drawings, and to help visualize relative relationships between the elements. For example, top and bottom surfaces are first and second surfaces that are opposite and removed from each other. A side surface is a third surface that extends between the first and second surfaces. Top, bottom, and side are not being used to define absolute physical positions.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

We claim:

1. An image capture unit comprising:
   a lengthwise axis;
   a first circuit board;
   a first imaging assembly having
      a bottom surface mounted on a surface of a portion of the first circuit board, and
      a top surface opposite the bottom surface of the first imaging assembly;
   a second circuit board; and
   a second imaging assembly having
      a bottom surface mounted on a surface of a portion of the second circuit board, and
      a top surface opposite the bottom surface of the second imaging assembly;
   wherein the portion of the first circuit board and the portion of the second circuit board have a stacked configuration in which the top surface of the first imaging assembly and the top surface of the second imaging assembly face each other and are approximately parallel to and on opposite sides of the lengthwise axis.

2. The image capture unit of claim 1:
   wherein an end of another portion of the first circuit board is adjacent to an end of another portion of the second circuit board;
   wherein the first imaging assembly is further mounted on the another portion of the first circuit board; and
   wherein the second imaging assembly being mounted on the second circuit board is further mounted on the another portion of the second circuit board.

3. The image capture unit of claim 1:
   the first circuit board comprising: a first rigid circuit board portion, a flex circuit board portion, and a second rigid circuit board portion, the flex circuit board portion being positioned between the first rigid circuit board portion and the second rigid circuit board portion, and the portion of the first circuit board being the first rigid circuit board portion; and
   the second circuit board comprising: a first rigid circuit board portion, a flex circuit board portion, and a second rigid circuit board portion, the flex circuit board portion of the second circuit board being positioned between the first rigid circuit board portion of the second circuit board and the second rigid circuit board portion of the second circuit board, and the portion of the second circuit board being the first rigid circuit board portion of the second circuit board.

4. The image capture unit of claim 3, comprising:
   wherein the second rigid circuit board portion of the first circuit board and the second rigid circuit board portion of the second circuit board are approximately perpendicular to the lengthwise axis of the image capture unit.

5. The image capture unit of claim 1, further comprising:
   a first objective lens system configured to focus a first image on the first imaging assembly; and
   a second objective lens system configured to focus a second image on the second imaging assembly.

6. The image capture unit of claim 1 further comprising:
   a window having a surface, wherein the surface of the window is at an angle to the lengthwise axis of the image capture unit.

7. The image capture unit of claim 1 further comprising:
   a frame having mounted therein the first and second imaging assemblies and the first and second circuit boards, where at least one of the first and second circuit boards is hermetically sealed to the frame.

8. The image capture unit of claim 1 further comprising:
   a support wall, and a wall;
   the first circuit board having a metal trace and an outer perimeter, the metal trace being around the outer perimeter;
   the support wall being affixed to the metal trace to form a hermetic seal; and
   the support wall being affixed to the wall.

9. The image capture unit of claim 8, wherein the support wall is affixed to the metal trace by a solder joint.

10. The image capture unit of claim 8, wherein the support wall is affixed to the wall by an electro-weld.

11. The image capture unit of claim 3, each of the flex circuit board portions being configured in a right angle bend.

12. The image capture unit of claim 1, each of the first circuit board and the second circuit board including at least one sacrificial layer.

* * * * *